United States Patent [19]

Chen et al.

[11] Patent Number: 5,782,828
[45] Date of Patent: Jul. 21, 1998

[54] ABLATION CATHETER WITH MULTIPLE FLEXIBLE CURVES

[75] Inventors: Peter Cheng Chen, Irvine; Alan de la Rama, Cerritos, both of Calif.

[73] Assignee: Irvine Biomedical, Inc., Irvine, Calif.

[21] Appl. No.: 763,614

[22] Filed: Dec. 11, 1996

[51] Int. Cl.⁶ ............................................. A61B 17/36
[52] U.S. Cl. ............................ 606/42; 607/122; 607/102; 606/41; 604/95
[58] Field of Search ................... 606/41, 42, 45–50; 604/22, 95; 600/370–374; 607/100–102, 122

[56] References Cited

U.S. PATENT DOCUMENTS

| | | |
|---|---|---|
| 4,723,936 | 2/1988 | Buchhinder et al. . |
| 4,753,223 | 6/1988 | Bremer ............................... 604/95 |
| 4,960,134 | 10/1990 | Webster, Jr. . |
| 4,998,916 | 3/1991 | Hammerslag et al. . |
| 5,098,431 | 3/1992 | Rydell ............................... 606/48 |
| 5,190,050 | 3/1993 | Nitzsche . |
| 5,263,493 | 11/1993 | Avitall ............................... 607/122 |
| 5,295,484 | 3/1994 | Marcus et al. . |
| 5,313,943 | 5/1994 | Houser et al. . |
| 5,358,479 | 10/1994 | Wilson . |
| 5,368,564 | 11/1994 | Savage . |
| 5,389,073 | 2/1995 | Imran . |
| 5,395,327 | 3/1995 | Lundquist et al. ................. 604/95 |
| 5,397,321 | 3/1995 | Houser et al. . |
| 5,409,000 | 4/1995 | Imran . |
| 5,487,757 | 1/1996 | Truckai et al. . |
| 5,531,686 | 7/1996 | Lundquist et al. . |
| 5,545,200 | 8/1996 | West et al. ........................ 607/122 |
| 5,582,609 | 12/1996 | Swanson et al. ................... 607/122 |
| 5,617,854 | 4/1997 | Munsif ............................... 607/122 |
| 5,653,684 | 8/1997 | Laptewicz et al. ............... 604/22 |

*Primary Examiner*—Michael Peffley

[57] ABSTRACT

An electrophysiology catheter suitable for radiofrequency ablation of cardiac tissue endocardially or epicardially comprises a catheter shaft whereby a distal tip section having multiple steerable curved portions, multiple long electrodes and multiple temperature sensors, further comprising a close-loop control mechanism for each electrode with a temperature sensor.

7 Claims, 4 Drawing Sheets

ABLATION CATHETER WITH MULTIPLE FLEXIBLE CURVES

FIELD OF THE INVENTION

The present invention generally relates to improved constructions for cardiovascular ablation catheters. More particularly, this invention relates to methods and apparatus for controlling cardiac arrhythmias via a cardiovascular catheter having multiple flexible curves and multiple ablating electrodes in conjunction with temperature control mechanisms for ablation endocardial or epicardial tissues simultaneously or in series.

BACKGROUND OF THE INVENTION

Abnormal heart rhythms are generally referred to as cardiac arrhythmias, with an abnormally rapid heart beat being referred to as a tachycardia. The present invention is concerned with the treatment of tachycardias which are frequently caused by the presence of an "arrhythmogenic site" or "atrioventricular accessory pathway" close to the inner or outer surface of the upper chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Catheter-based treatments, in contrast, will actually cure the problem, usually by ablating the abnormal arrhythmogenic tissue or accessory pathways responsible for the tachycardia. It is important for a physician to accurately steer the catheter to the exact site for ablation.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathways are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal conducted signal patterns responsible for the tachycardia can be eliminated. However, in the case of atrial fibrillation (AFib), multiple arrhythmogenic sites and/or multiple accessory pathways exist. The conventional catheter with a single ablation tip electrode can not effectively cure this arrhythmia.

Atria Fibrillation is believed to be the result of aberrant conduction of electrical signals within the atria, resulting in a condition in which the transmission of electrical activity becomes so disorganized that the atria contracts quiveringly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

In a conventional electrophysiology procedures, a catheter is inserted into a major vein or artery, usually in the neck or groin area. The tip section of a catheter is referred to here as the portion of that catheter shaft containing the electrodes which is either a fixed curve or deflectable. The catheter is then guided into chambers of the heart by appropriate manipulation through the vein or artery. The tip of a catheter must be manipulatable by a physician from the proximal end of the catheter, so that the electrodes at the tip section can be positioned against the tissue site, even at a curved location, to be ablated. The catheter must have multiple electrodes and multiple flexible curves in order to be placed in the endocardial edge at the entrance region from the aorta to the heart chamber. The tip section of a conventional electrophysiology catheter that is deflectable usually contains a tip section that forms only a curve for ablation purpose. A temperature sensor is usually attached on the tip electrode.

Steerable catheters are known for use in a variety of medical procedures. For example, see U.S. Pat. No. 5,395,328 to Ockuly, U.S. Pat. No. 5,391,147 to Imran, U.S. Pat No. 5,383,923 to Webster Jr., U.S. Pat. No. 5,368,564 to Savage, U.S. Pat. No. 5,358,479 to Wilson, U.S. Pat. No. 5,322,064 to Lundquist, U.S. Pat No. 4,960,134 to Webster, Jr., U.S. Pat No. 4,944,727 to McCoy, U.S. Pat. No. 4,826,087 to Chinery, U.S. Pat. No. 4,685,457 to Donenfeld, U.S. Pat No. 3,605,725 to Bentov, and U.S. Pat No. 3,470,876 to Barchilon. Typically, such catheter employs a steering wire, extending from a steering control mechanism at the proximal end of the catheter to an anchor point at the distal end of the catheter. A flat wire or the like that provides an anchor point for the steering wire is usually extended through the catheter shaft to cause the catheter to bend in a circle fashion, avoiding buckling or collapsing. By tensioning certain of the steering wire from the proximal handle, the tip of the catheter can be manipulated in a desired direction, but in a single circle fashion. While radiofrequency catheter ablation using current catheter design has produced promising results, the known catheter usually has only one large electrode and has only one curve for ablation purpose. In the AFib patient, because of the simultaneous occurrence of multiple wavelets of re-entry electrical impulses within the atria, it is necessary to stop the multiple re-entry impulses simultaneously through the creating of linear lesion endocardially and epicardially. Recent literature reported an ablation catheter having a large electrode was introduced to ablate the epicardial arrhythmogenic sites. However, due to the particular anatomic exterior structure of the heart, it is very difficult for the catheter with a single curve to make good contact with the epicardial tissue in order to deliver RF energy during ablation. It is the purpose of this invention to develop a new ablation catheter that provides multiple flexible curves on the distal portion of the catheter to accommodate the anatomic structure of the atrium and the epicardial surface.

This particular feature allows the multiple ablation electrodes to make better contact with the endocardial atrial tissue and the epicardial tissue to create large lesion and/or linear lesion.

SUMMARY OF THE INVENTION

The present invention provides an improved ablation catheter which can be used in ablating multiple arrhythmogenic tissue or accessory pathways of a heart. This catheter is particularly useful for treating the atrial fibrillation (AFib) from the endocardial or epicardial sides. In one embodiment, an ablation electrophysiology catheter comprises a catheter shaft having a distal section, a proximal end, a distal end, and at least one lumen extending therebetween, wherein a plurality of long electrodes are disposed on the distal section, and wherein the distal section is deflectable; a plurality of temperature sensors located to the said plurality of long electrodes; and a handle attached to the proximal end of the said catheter shaft. The multiple flexible curves are essential to ensure that the multiple ablation electrodes are making good contact with the atrial endocardium during ablation or to conform to the epicardial tissue surface. This requirement is of particular importance in creating large, linear or contiguous lesions for treating AFib. Lesions generated by this multiple flexible curved catheter can also create an electrical maze pattern of the same type resulting from a surgical procedure for treating AFib. Without good contact between the ablation electrodes and the target tissue, the interface impedance can rise to a very high value to either require the delivery of extra RF energy or to cut off the RF energy delivery. Without good contact between the ablation electrodes and the target tissue, the multiple temperature sensors embedded on the ablation electrodes will not be able to monitor the tissue contact temperature during RF energy delivery. This is also very important in controlling the safety and efficacy of RF ablation, because the size of lesion is a function of the amount of RF energy delivery, ablation duration and local temperature rise.

In other embodiment, an ablation catheter further comprises a close-loop control mechanism for each electrode having a temperature sensor. An ablation catheter of this invention further comprises RF energy delivery. To better control the desired lesion, more RF energy may be needed when the measured tissue contact temperature is relatively low. On the other hand, less RF energy is needed when a relatively high tissue contact temperature is detected. In still another embodiment, an ablation catheter further comprises a programmed control mechanism for independently selecting and controlling the ablation electrodes of the catheter system. In this case, it further comprises selecting and controlling the number of electrodes ablated simultaneously or sequentially.

In another alternate embodiment, an ablation catheter comprises the ablation electrodes of longer than 2 mm in length, preferably 4 to 10 mm. It further comprises the number of ablation electrodes of more than 2, preferably more than 10. The material for electrodes at the tip section may be consisted of noble metals such as platinum, iridium, gold, silver, or alloy of their mixture.

To enhance biocompatibility, the ablation catheter further comprises surface coating of heparin, hirudin, antibiotics, or the like on the said plurality of long electrodes of the catheter shaft. In a further embodiment, an ablation catheter further comprises surface coating of low surface energy substrates, such as Teflon® type fluorinated polymers, on the surface of catheter shaft to mitigate blood coagulation during high energy ablation. Fluorinated polymer can be deposited on the shaft surface via plasma coating technology. The low surface energy in this case is lower than that of the blood vessel or the endocardial tissue.

A method for operating an ablation catheter having multiple steerable curved portions, multiple long electrodes and multiple temperature sensors at its tip section within a heart chamber comprises percutaneously introducing the distal end of a catheter through a blood vessel to the heart chamber, wherein the first curved portion for securing the catheter tip around the coronary sinus, and the second and third curved portions to fit a side of a mitral annulus location. In a further embodiment, a method for operating an ablation catheter further comprises a close-loop control mechanism for each electrode having a temperature sensor. In still another embodiment, a method for operating an ablation catheter further comprises a programmed control mechanism for independently selecting and controlling the ablation electrodes and the number of electrodes ablated simultaneously or sequentially.

Another method for operating an ablation catheter having multiple steerable curved portions, multiple long electrodes and multiple temperature sensors at its tip section epicardially comprises percutaneously introducing the distal end of a catheter through a surgical opening at the chest, leading the catheter tip piercing through the pericardium, and directing the tip section to intimately contact the epicardial tissue surface having multiple curvatures. In a further embodiment, a method for operating an ablation catheter further comprises a close-loop control mechanism for each electrode having a temperature sensor. In another embodiment, a method for operating an ablation catheter further comprises a programmed control mechanism for independently selecting and controlling the ablation electrodes and the number of electrodes ablated simultaneously or in series.

The method and apparatus of the present invention have several significant advantages over known catheters or ablation techniques, particularly the multiple steerable curved portions, multiple large ablation electrodes, multiple temperature sensors and a close-loop control mechanism independently for each electrode at the tip section.

DETAILED DESCRIPTION OF EXEMPLARY EMBODIMENTS

Figure 1:
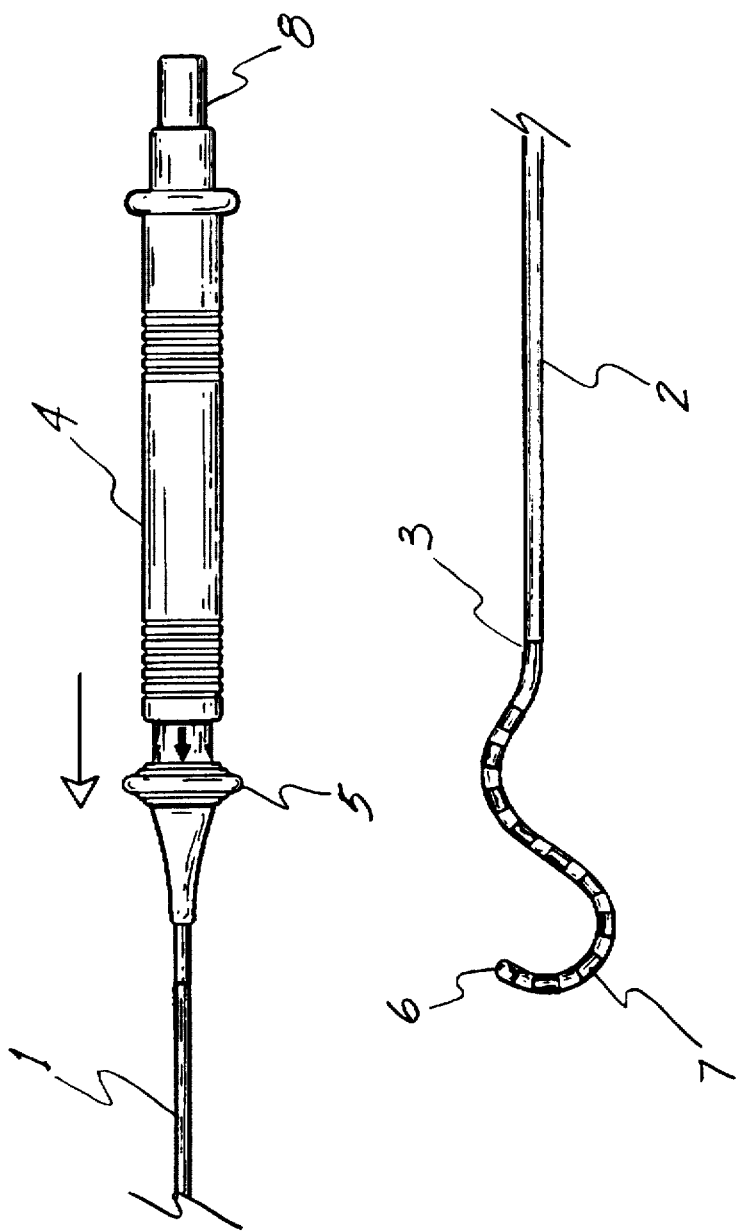
FIG. 1 is a side view of the catheter of this invention.

Referring to FIG. 1, a steerable ablation catheter system 1 constructed in accordance with the principles of the present invention comprises: a catheter shaft 2 having a tip section 3 and proximal handle 4. The tip section may form more than one curved portion. More than one long electrode available for ablation use are disposed on the tip section. The tip section 3 is deflectable by using a controlling ring 5 at the handle 4 for the steering purpose. By pushing the controlling ring 5 forward, the tip section 3 forms multiple curved portions in one plane. By pulling the controlling ring 5 to its neutral position, the above-mentioned multiple curvings are reversed and the tip section becomes straight. As shown in FIG. 1, the long tip electrode 6 and a plurality of long band electrodes 7 may be placed in the tip section. Each electrode is connected to a conducting wire, passing through the lumen of the catheter shaft 2, and is soldered to a pin of the connector end 8. The conducting wire from connector end 8 is externally connected to an EKG monitor for monitoring intracardiac or epicardial signals during electrophysiology mapping procedure or to a radiofrequency energy generator during an ablation procedure. From there, the RF energy is transmitted through the wire to the individual ablation electrode and is delivered to the contact tissue. A temperature sensor, either a thermocouple or a thermister, is embedded in each electrode to measure the tissue contact temperature when RF energy is delivered. The temperature sensing wire from the thermocouple or thermister is externally connected to a temperature measuring circuit inside the RF generator. The temperature reading is thereafter relayed to a close-loop control mechanism to adjust the RF energy output. The RF energy delivered is thus controlled by the temperature sensor reading or by the pre-programmed control algorithm.

Figure 2:
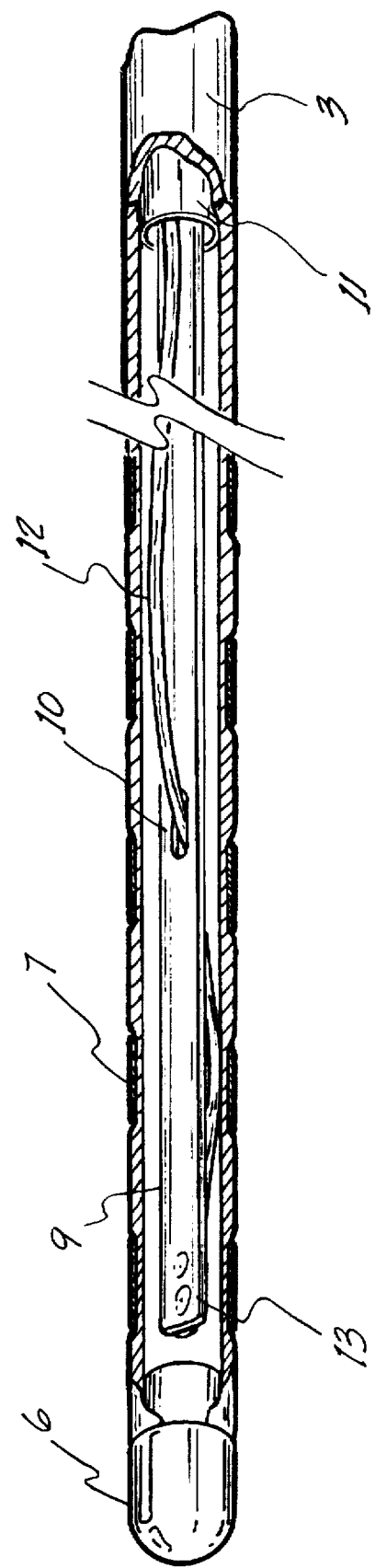
FIG. 2 is a cross-sectional view of the tip section of FIG. 1.

In one embodiment of this invention, the means for deflecting the distal tip section of a catheter comprises at least one steering wire along with a flat planar wire. Referring to FIG. 2, a flat planar wire 9 with a small slot 10 at a pre-determined location is mounted inside the catheter shaft at the supporting point 11. One end of a steering wire 12 is securely attached to the distal point of the flat planar wire 9 at an anchor point 13. The steering wire 12 passing through the slot 10 is connected to the controlling mechanism at the handle. A means is provided at the proximal handle for selectively applying tension to the steering wire to cause multiple deflections of the deflectable tip section. The steering wire is located offset on the other side of the flat planar wire as referred to the anchor point 13.

Figure 3:
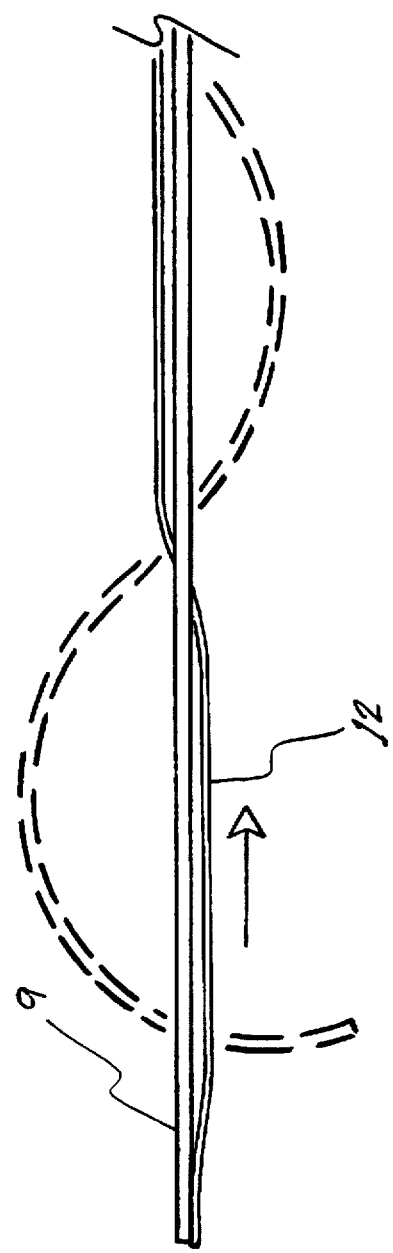
FIG. 3 shows one mechanism of forming multiple curved portions of a catheter of this invention.

As shown in FIG. 3, when the steering wire 12 is pulled, the portion of the tip section 3 distal to the slot 10 of the catheter shaft 2 bends for form a deflectable curve by yielding to the pulling force of the pulling wire 12. The angle and diameter of the shaft bending curve is a function of the pulling distance and the slot location 10 on the flat planar wire 9. Simultaneously, the second curve forms at the portion of the tip section proximal to the slot 10 of the shaft 2, said second curve being at the opposite side of the first tip curve. By designing the slot location on the flat planar wire, the relative curve sizes of the multiple curved catheter can be controlled.

Figure 4:
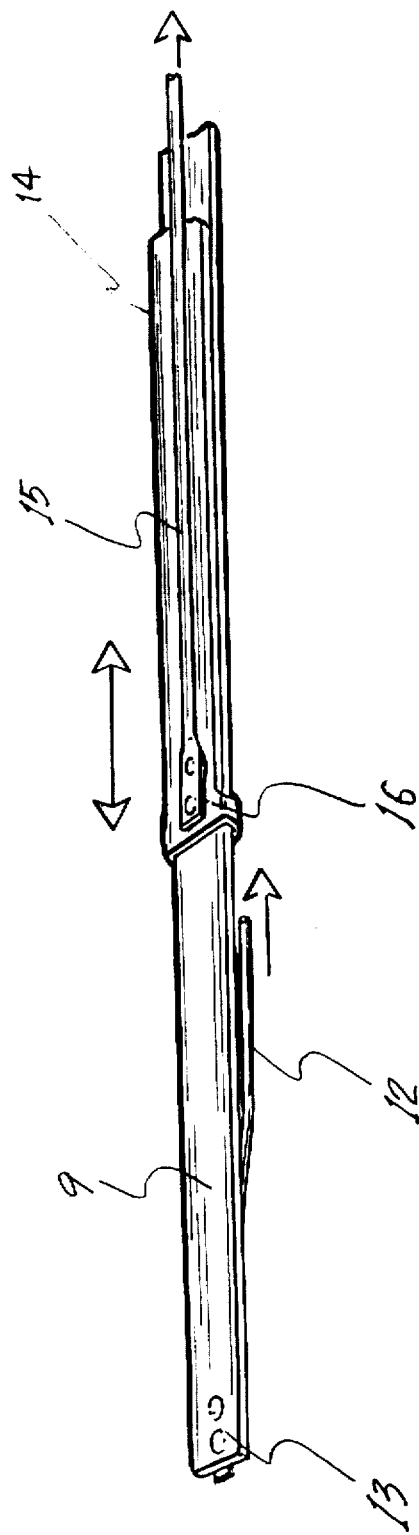
FIG. 4 shows an alternate mechanism of forming multiple curved portions of a catheter of this invention.

FIG. 4 shows an alternate variation of the flat planar wire design to effect various bending curves in the said multiple curved catheter invention. In this alternate embodiment, a secondary flat wire 14 is mounted freely on the prior primary flat planar wire 9. A new secondary steering wire 15 is then attached on this secondary flat wire 14 at point 16. By pulling said secondary pulling wire 15, a second curve is formed at the tip section of the shaft. The secondary flat wire 14 may be moveable up and down freely along the primary flat wire 9. The primary pulling wire 12 which is anchored at the far distal end 13 of the primary flat wire 9 is used to control the pulling in one direction to form the distal curve. By controlling the location of the secondary flat wire 14, the curve diameters of the distal curve and the second curve can be semi-independently controlled.

From the foregoing, it should now be appreciated that an improved ablation catheter having multiple steerable curved portions, multiple temperature sensors, multiple ablation electrodes and a close-loop control mechanism has been disclosed for treating atrial arrhythmias. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An ablation catheter comprising:

(a) a catheter shaft having a distal section, a proximal end, a distal end, and at least one lumen extending therebetween, wherein a plurality of long electrodes are disposed on the distal section, and wherein the distal section is deflectable;

(b) a plurality of temperature sensors located on the plurality of long electrodes;

(c) a programmed control mechanism connected to the plurality of temperature sensors and the plurality of long electrodes for independently selecting and control energy delivery to each of the long electrodes;

(d) a handle attached to the proximal end of the catheter shaft;

(e) a steering mechanism disposed on the handle, wherein the steering mechanism comprises one steering wire and one flat planar wire, wherein at least one slot is positioned at predetermined positions on the flat planar wire, and wherein the steering wire passes through at least one of the slots;

(f) a means on the steering mechanism at the handle for selectively applying tension to the steering wire to cause a plurality of consecutive deflections of the distal section, wherein a next consecutive deflection is on an opposite side of the flat planar wire relative to a prior deflection;

(g) a means connected to the programmed control mechanism and the plurality of long electrodes for delivering RF energy from an external RF generator to each of the plurality of long electrodes, wherein the RF energy delivery to each of the long electrodes is done in one of a simultaneous or sequential mode.

2. An ablation catheter as in claim 1, further comprising at least two consecutive deflections of the distal section.

3. An ablation catheter as in claim 1, further comprising a surface coating of heparin, hirudin, a antibiotics on the plurality of long electrodes of the catheter to enhance biocompatibility.

4. An ablation catheter as in claim 1, further comprising a coating of low surface energy substrates on a surface of the catheter shaft to mitigate blood coagulation during high energy ablation.

5. A method for operating an ablation catheter, the catheter comprising a catheter shaft having a distal section, a proximal end, a distal end, and at least one lumen extending therebetween, wherein a plurality of long electrodes are disposed on the distal section, and wherein the distal section is deflectable, a plurality of temperature sensors located on the plurality of long electrodes, a handle attached to the proximal end of the catheter shaft, a steering mechanism disposed on the handle, wherein the steering mechanism comprises one steering wire and one flat planar wire, wherein at least one slot is positioned at pre-determined locations on the flat planar wire, and wherein the steering wire passes through the at least one slot, and means on the steering mechanism at the handle for selectively applying tension to the steering wire to cause a plurality of consecutive deflections of the distal section, wherein a next consecutive deflection is on an opposite side of the flat planar wire relative to a prior deflection, the method comprising the steps of:

(a) percutaneously introducing the distal end of the catheter through a blood vessel to the heart chamber, wherein a first of the consecutive deflections of the catheter is positioned around the coronary sinus;

wherein a second of the consecutive deflections is positioned to fit a side of a mitral annulus location; and (b) delivering RF energy from an external RF generator to each of the plurality of long electrodes, wherein the RF energy delivery to each of the plurality of long electrodes is done in one of a simultaneous or a sequential mode.

6. A method for operating an ablation catheter as in claim 5, further comprising providing a surface coating of heparin, hirudin, or antibiotics on the plurality of long electrodes of the catheter to enhance biocompatibility.

7. A method for operating an ablation catheter as in claim 5, further comprising providing a surface coating of low surface energy substrates on a surface of the catheter shaft to mitigate blood coagulation during high energy ablation.

* * * * *